(12) United States Patent
Liu et al.

(10) Patent No.: US 11,653,890 B2
(45) Date of Patent: May 23, 2023

(54) SYSTEMS AND METHODS FOR IMAGE ACQUISITION

(71) Applicant: SHANGHAI UNITED IMAGING HEALTHCARE CO., LTD., Shanghai (CN)

(72) Inventors: Weiping Liu, Shanghai (CN); Xiaoyue Gu, Shanghai (CN); Shitao Liu, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 176 days.

(21) Appl. No.: 17/184,669

(22) Filed: Feb. 25, 2021

(65) Prior Publication Data

US 2021/0196224 A1 Jul. 1, 2021

Related U.S. Application Data

(63) Continuation of application No. 16/236,459, filed on Dec. 29, 2018, now Pat. No. 10,932,745, which is a
(Continued)

(30) Foreign Application Priority Data

Oct. 25, 2016 (CN) .......................... 201610937258.3

(51) Int. Cl.
*G06T 15/00* (2011.01)
*A61B 6/00* (2006.01)
(Continued)

(52) U.S. Cl.
CPC ............ *A61B 6/542* (2013.01); *A61B 5/0037* (2013.01); *A61B 5/72* (2013.01); *A61B 6/469* (2013.01);
(Continued)

(58) Field of Classification Search
CPC ..... A61B 5/0037; A61B 6/542; A61B 6/5235; A61B 2576/00; G06T 7/11; G06T 7/0012;
(Continued)

(56) References Cited

U.S. PATENT DOCUMENTS

2005/0135554 A1 6/2005 Mohr et al.
2007/0078339 A1 4/2007 Andress
(Continued)

FOREIGN PATENT DOCUMENTS

CN 105078495 A 11/2015
CN 105741303 A 7/2016
(Continued)

OTHER PUBLICATIONS

International Search Report in PCT/CN2017/107373 dated Jan. 19, 2018, 4 pages.
(Continued)

*Primary Examiner* — Brian Werner
(74) *Attorney, Agent, or Firm* — Metis IP LLC

(57) ABSTRACT

The present disclosure relates to a method and system for reducing radiation dose in image acquisition. The method may include obtaining first image data of a subject related to a first scan of the subject. The first scan may be of a first type of scan. The method may include reconstructing a first image of the subject based on the first image data and generating a dose plan of a second scan based on the first image. The second scan may be of a second type of scan. The method may also include obtaining second image data of the subject related to the second scan of the subject. The second scan may be performed according to the dose plan.

20 Claims, 11 Drawing Sheets

Related U.S. Application Data continuation of application No. PCT/CN2017/107373, filed on Oct. 23, 2017.

(51) Int. Cl.

| | |
|---|---|
| *A61B 5/00* | (2006.01) |
| *G06T 7/11* | (2017.01) |
| *G06T 7/73* | (2017.01) |
| *G06T 7/00* | (2017.01) |
| *G06T 11/00* | (2006.01) |
| *A61B 6/03* | (2006.01) |
| *A61B 6/12* | (2006.01) |
| *A61B 5/055* | (2006.01) |
| *G01R 33/48* | (2006.01) |

(52) U.S. Cl.
CPC .......... *A61B 6/5211* (2013.01); *A61B 6/5235* (2013.01); *A61B 6/5247* (2013.01); *G06T 7/0012* (2013.01); *G06T 7/11* (2017.01); *G06T 7/73* (2017.01); *G06T 11/003* (2013.01); *A61B 5/055* (2013.01); *A61B 6/032* (2013.01); *A61B 6/037* (2013.01); *A61B 6/12* (2013.01); *A61B 6/5217* (2013.01); *A61B 2576/00* (2013.01); *G01R 33/481* (2013.01); *G01R 33/4812* (2013.01); *G06T 2207/10072* (2013.01); *G06T 2207/30096* (2013.01)

(58) Field of Classification Search
CPC .............................. G06T 11/003–11/008; G06T 2207/10072–2207/10112; G06V 10/26; G06V 10/16; G06V 10/25
See application file for complete search history.

(56) References Cited

U.S. PATENT DOCUMENTS

| | | | |
|---|---|---|---|
| 2008/0242968 | A1 | 10/2008 | Claus et al. |
| 2009/0022386 | A1 | 1/2009 | Karau et al. |
| 2009/0238427 | A1 | 9/2009 | Hsieh et al. |
| 2012/0078089 | A1 | 3/2012 | Wollenweber et al. |
| 2013/0105699 | A1 | 5/2013 | Asma et al. |
| 2014/0119630 | A1 | 5/2014 | Sowards-Emmerd et al. |
| 2018/0360402 | A1* | 12/2018 | Carmi .................. G06T 7/0012 |
| 2019/0133544 | A1 | 5/2019 | Liu et al. |

FOREIGN PATENT DOCUMENTS

| | | |
|---|---|---|
| JP | 2005283421 A | 10/2005 |
| WO | 2018077141 A1 | 5/2018 |

OTHER PUBLICATIONS

Written Opinion in PCT/CN2017/107373 dated Jan. 19, 2018, 6 pages.
Extended European Search Report in European Application No. 17863864.9 dated Oct. 17, 2019, 6 pages.
First Office Action in Chinese Application No. 201610937258.3 dated Jan. 19, 2018, 28 pages.
Notice of Rejection in Japanese Application No. 2019-544961 dated Aug. 30, 2021, 11 pages.

* cited by examiner

SYSTEMS AND METHODS FOR IMAGE ACQUISITION

CROSS-REFERENCE TO RELATED APPLICATIONS

This application is a continuation of U.S. patent application Ser. No. 16/236,459, filed on Dec. 29, 2018, which is a continuation of International Application No. PCT/CN/2017/107373, filed on Oct. 23, 2017, which claims priority of Chinese Application No. 201610937258.3, filed on Oct. 25, 2016, the contents of each of which are incorporated herein by reference to its entirety.

TECHNICAL FIELD

The present disclosure generally relates to image acquisition, and more specifically relates to methods and systems for reducing radiation dose in image acquisition.

BACKGROUND

An anatomical image, such as a computed tomography (CT) image is commonly used in clinical diagnosis and medical research. An anatomical image of a subject can provide anatomical data of the subject, and be applied in attenuation correction of a functional image of the subject (e.g., a positron emission tomography (PET) image). However, in a CT scan, high dose radiations may be delivered to the subject (e.g., a patient or a portion thereof), which may be harmful for the subject to some extent. Thus, it is desirable to provide systems and methods for reducing radiation dose in CT image acquisition.

SUMMARY

In an aspect of the present disclosure, a method is provided. The method may include obtaining first image data of a subject related to a first scan of the subject. The first scan may be of a first type of scan. The method may also include reconstructing a first image of the subject based on the first image data and generating a dose plan of a second scan based on the first image. The second scan may be of a second type of scan. The method may further include obtaining second image data of the subject related to the second scan of the subject. The second scan may be performed according to the dose plan.

In some embodiments, the first type of scan may be at least one of a positron emission tomography (PET) scan, a single photon emission computed tomography scan (SPETC), or a magnetic resonance (MR) scan.

In some embodiments, the second type of scan may be a computed tomography (CT) scan.

In some embodiments, the determining the dose plan of the second scan based on the first image may include determining at least one lesion in the first image. The determining the dose plan of the second scan may also include determining at least one region of interest (ROI) in the first image based on the at least one lesion. The at least one ROI may enclose the at least one lesion. The determining the dose plan of the second scan may further include determining the dose plan of the second scan based on the at least one ROI. The dose plan may include a first dose corresponding to the ROI and a second does corresponding to a region outside the ROI, and the first dose may be higher than the second dose.

In some embodiments, the determining the at least one ROI in the first image may include determining at least one candidate ROI in the first image based on the at least one lesion. The at least one candidate ROI may enclose at least one lesion. The determining the at least one ROI in the first image may also include determine a coordinate range of the at least one candidate ROI along an axial direction, and determining the at least one ROI in the first image based on the coordinate range of the at least one candidate ROI along the axial direction.

In some embodiments, the method may further include reconstructing a second image of the subject based on the second image data, and correcting the first image based on the second image to generate a corrected first image.

In some embodiments, the correcting the first image based on the second image may include performing an attenuation correction on the first image based on the second image.

In some embodiments, the method may further include reconstructing a second image of the subject based on the second image data, correcting the first image based on the second image, and generating a fourth image based on the corrected first image and the second image by fusing the corrected first image and the second image.

In some embodiments, the first scan may have a first scan duration. The method may further include obtaining third image data of the subject related to a third scan of the subject. The third scan may be of the first type of scan and have a second scan duration. The second scan duration may be longer than the first scan duration. The method may further include reconstructing a third image based on the third image data and generating a fourth image based on the third image and the second image data.

In another aspect of the present disclosure, a system is provided. The system may include at least one storage device storing a set of instructions and at least one processor in communication with the at least one storage device. When the at least one processor executes the set of instructions, the at least one processor may be configured to cause the system to obtain first image data of a subject related to a first scan of the subject. The first scan may be of a first type of scan. The at least one processor may be also configured to cause the system to reconstruct a first image of the subject based on the first image data, and generate a dose plan of a second scan based on the first image. The second scan may be of a second type of scan. The at least one processor may be further configured to cause the system to obtain second image data of the subject related to the second scan of the subject. The second scan may be performed according to the dose plan.

In yet another aspect of the present disclosure, a non-transitory computer readable medium including executable instructions is provided. When the executable instructions are executed by at least one processor, the non-transitory computer readable medium may cause the at least one processor to effectuate a method. The method may include obtaining first image data of a subject related to a first scan of the subject. The first scan may be of a first type of scan. The method may also include reconstructing a first image of the subject based on the first image data and generating a dose plan of a second scan based on the first image. The second scan may be of a second type of scan. The method may further include obtaining second image data of the subject related to the second scan of the subject. The second scan may be performed according to the dose plan.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 2:
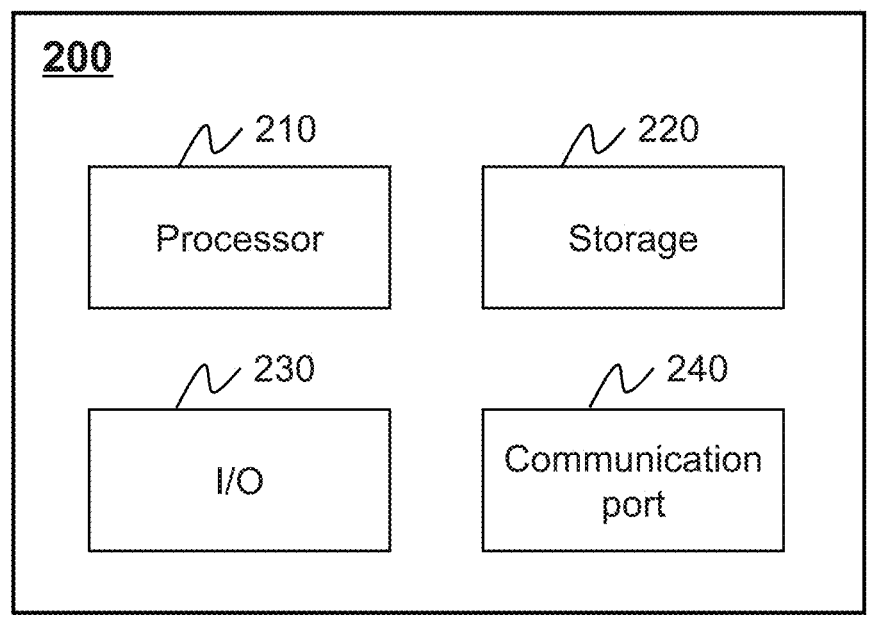
FIG. 2 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging, such as for disease diagnosis or research purposes. In some embodiments, the imaging system may be a computed tomography (CT) system, a magnetic resonance imaging (MRI) system, a positron emission tomography (PET) system, a Single Photon Emission Computed Tomography (SPECT), or the like, or any combination thereof. In some embodiments, the imaging system may be a multi-modality imaging system such as PET/CT system, a SPECT/CT system, a PET/MRI system, a SPECT/MRI system, etc.

The term "image" used in this disclosure may refer to a 2D image, a 3D image, a 4D image, and/or any related image data (e.g., image data, projection data corresponding to the image data). The term "region of interest (ROI)" used in this disclosure may refer to a region in an image of a subject. An ROI may correspond to a physical portion (e.g., a tissue, an organ) of the subject. This is not intended to limit the scope of the present disclosure. For persons having ordinary skills in the art, a certain amount of variations, changes, and/or modifications may be deducted under the guidance of the present disclosure. Those variations, changes, and/or modifications do not depart from the scope of the present disclosure.

The present disclosure relates to systems and methods for reducing radiation dose in image acquisition. The system may acquire first image data of a subject and reconstruct a first image based on the first image data. The first image data and the first image may include functional data of the subject. For example, the first image data may include PET data and the first image may be a PET image of the subject. The system may generate a dose plan of a second scan (e.g., a CT scan) based on the first image. The first image may indicate conditions of different portions of the subject and the dose plan may include various doses corresponding to different portions of the subject. For example, the dose may include a low dose corresponding to normal portions of the subject and a high dose corresponding to abnormal portions (e.g., portions that include lesions or potentially lesions). As such, the normal portions of the subject may be prevented from receiving unnecessary radiations. The system may further acquire second image data (e.g., CT image data) based on the second scan performed according to the dose plan, and reconstruct a second image (e.g., CT image) based on the second image data. The second image may include anatomical data of the subject and may be applied in attenuation correction of the first image.

Figure 1:
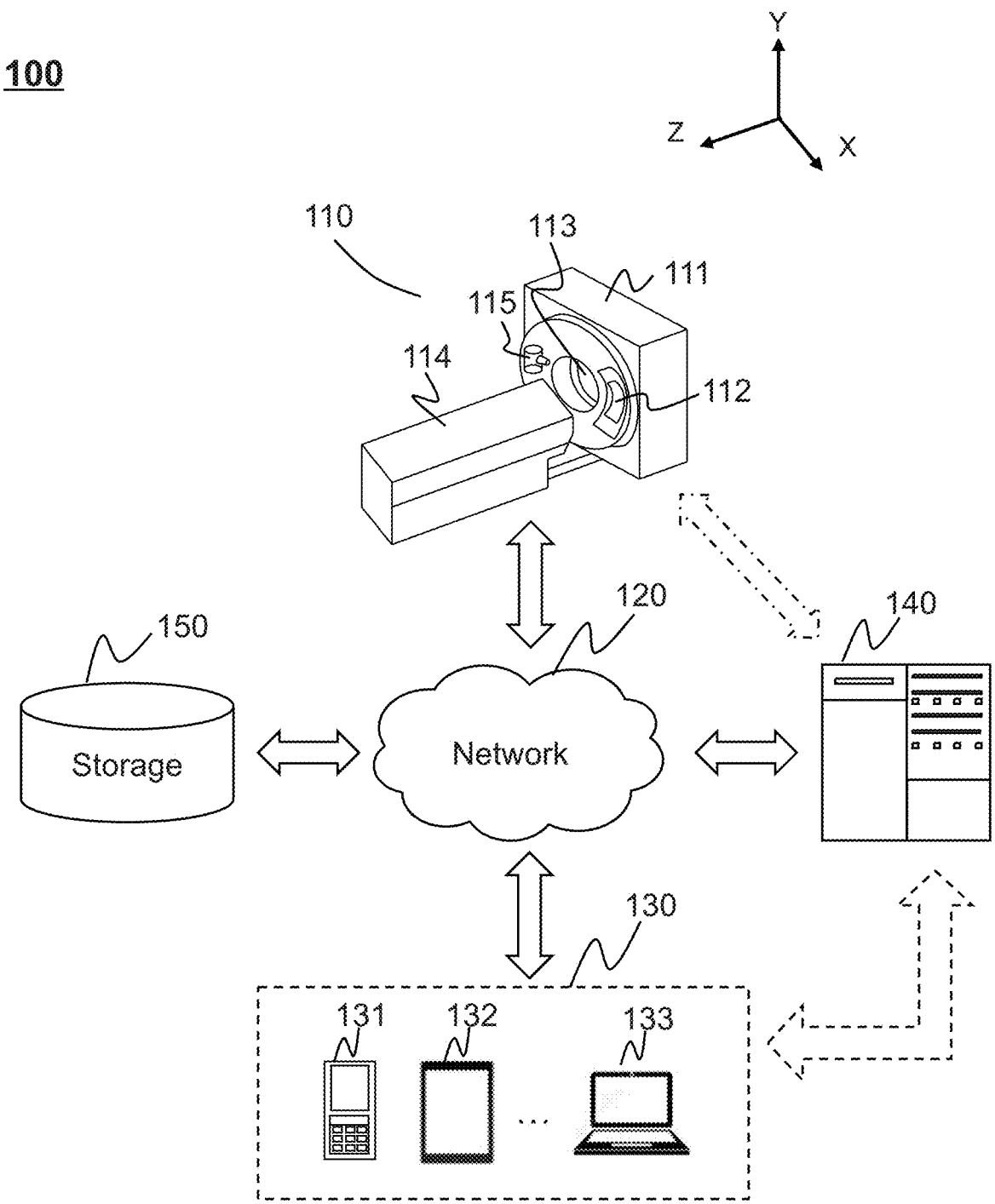
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. As shown, the imaging system 100 may include a scanning device 110, a network 120, one or more terminals 130, a processing engine 140, and a storage device 150.

The scanning device 110 may be configured to scan a subject to acquire data related to the subject. In some embodiments, the scanning device 110 may be configured to acquire functional data of the subject. For example, the scanning device 110 may be a PET device, a SPETCT, or an MRI device. In some embodiments, the scanning device 110 may be configured to acquire anatomical data of the subject. For example, the scanning device 110 may be a CT device. In some embodiments, the scanning device 110 may be configured to acquire functional data and anatomical data of the subject. For example, the scanning device 110 may be a combined scanning device, such as a PET/CT device, an MRI/CT device, or a SPECT/CT device.

Merely by way of example, the scanning device 110 may be a PET/CT device. The scanning device 110 may include a gantry 111, a detector 112, a detecting region 113, a table 114, and a radioactive scanning source 115. The gantry 111 may support the detector 112 and the radioactive scanning source 115. A subject may be placed on the table 114 for scanning. The table 114 may be moved into the detection tunnel of the scanning device 110 along the Z-axis (also referred to as the axial direction) as illustrated in FIG. 1. The subject may be positioned at different positions for a CT scan and a PET scan by adjusting the table 114. The radioactive scanning source 115 may emit radioactive rays to the subject. The detector 112 may include a PET detector and a CT detector. The PET detector may detect radiation events (e.g., gamma photons) emitted from the detecting region 113. The CT detector may detect radiations emitted from the radioactive scanning source 115. In some embodiments, the detector 112 may include one or more detector units. The detector units may include a scintillation detector (e.g., a cesium iodide detector), a gas detector, etc. The detector unit may be and/or include a single-row detector and/or a multi-rows detector.

The network 120 may include any suitable network that can facilitate exchange of information and/or data for the imaging system 100. In some embodiments, one or more components of the imaging system 100 (e.g., the scanning device 110, the terminal 130, the processing engine 140, the storage device 150, etc.) may communicate information and/or data with one or more other components of the imaging system 100 via the network 120. For example, the processing engine 140 may obtain image data from the scanning device 110 via the network 120. As another example, the processing engine 140 may obtain user instructions from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, witches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal(s) 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing engine 140.

The processing engine 140 may process data and/or information obtained from the scanning device 110, the terminal 130, and/or the storage device 150. For example, the processing engine 140 may generate a dose plan for a CT scan based on a PET image. In some embodiments, the processing engine 140 may be a single server or a server group. The server group may be centralized or distributed. In some embodiments, the processing engine 140 may be local or remote. For example, the processing engine 140 may access information and/or data stored in the scanning device 110, the terminal 130, and/or the storage device 150 via the network 120. As another example, the processing engine 140 may be directly connected to the scanning device 110, the terminal 130 and/or the storage device 150 to access stored information and/or data. In some embodiments, the processing engine 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing engine 140 may be implemented by a computing device 200 having one or more components as illustrated in FIG. 2.

The storage device 150 may store data, instructions, and/or any other information. In some embodiments, the storage device 150 may store data obtained from the terminal 130 and/or the processing engine 140. In some embodiments, the storage device 150 may store data and/or instructions that the processing engine 140 may execute or use to perform exemplary methods described in the present disclosure. In some embodiments, the storage device 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components in the imaging system 100 (e.g., the processing engine 140, the terminal 130, etc.). One or more components in the imaging system 100 may access the data or instructions stored in the storage device 150 via the network 120. In some embodiments, the storage device 150 may be directly connected to or communicate with one or more other components in the imaging system 100 (e.g., the processing engine 140, the terminal 130, etc.). In some embodiments, the storage device 150 may be part of the processing engine 140.

FIG. 2 is a schematic diagram illustrating exemplary hardware and/or software components of an exemplary computing device 200 on which the processing engine 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing engine 140 in accordance with techniques described herein. The computer instructions may include, for example, routines, programs, objects, components, data structures, procedures, modules, and functions, which perform particular functions described herein. For example, the processor 210 may process image data obtained from the scanning device 110, the terminal 130, the storage device 150, and/or any other component of the imaging system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both step A and step B, it should be understood that step A and step B may also be performed by two or more different processors jointly or separately in the computing device 200 (e.g., a first processor executes step A and a second processor executes step B, or the first and second processors jointly execute steps A and B).

The storage 220 may store data/information obtained from the scanning device 110, the terminal 130, the storage device 150, and/or any other component of the imaging system 100. In some embodiments, the storage 220 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing engine 140 for determining a regularization item.

The I/O 230 may input and/or output signals, data, information, etc. In some embodiments, the I/O 230 may enable a user interaction with the processing engine 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing engine 140 and the scanning device 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
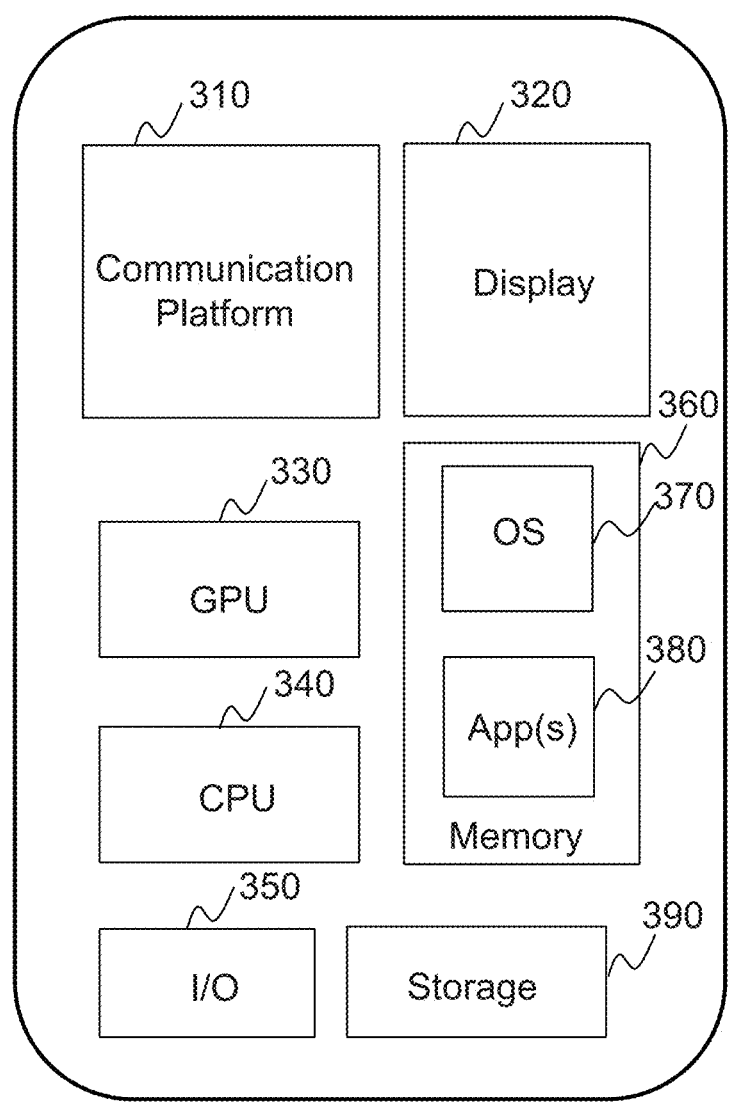
FIG. 3 is a schematic diagram illustrating exemplary hardware and/or software components of a mobile device according to some embodiments of the present disclosure.

FIG. 3 is a schematic diagram illustrating exemplary hardware and/or software components of a mobile device 300 on which the terminal 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing engine 140. User interactions with the information stream may be achieved via the I/O 350 and provided to the processing engine 140 and/or other components of the imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
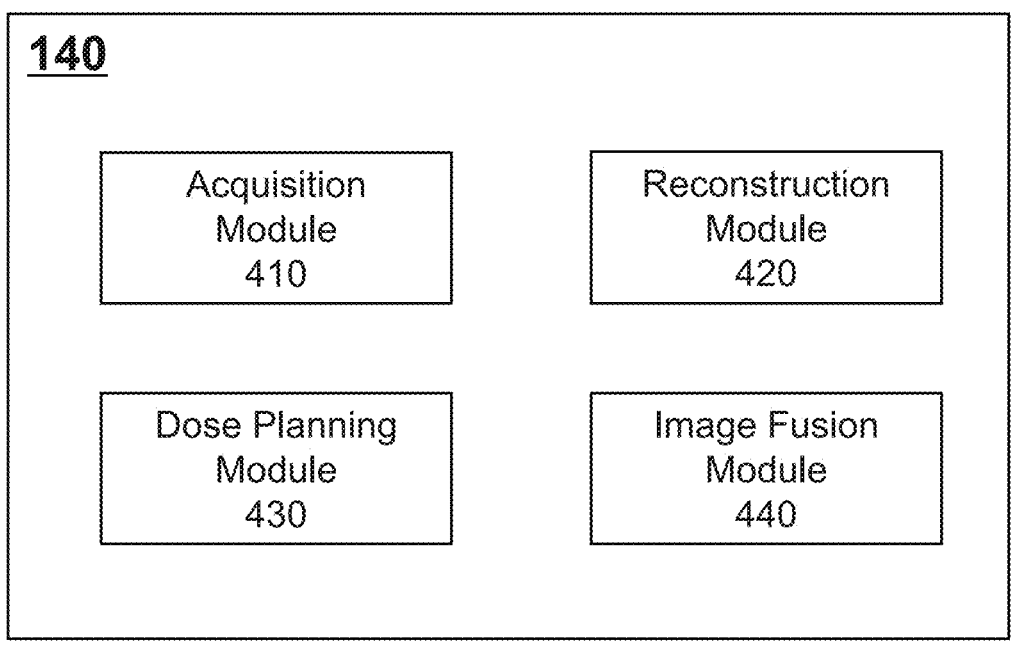
FIG. 4 is a block diagram illustrating an exemplary processing engine according to some embodiments of the present disclosure.

FIG. 4 is a block diagram illustrating an exemplary processing engine 140 according to some embodiments of the present disclosure. The processing engine 140 may include an acquisition module 410, a reconstruction module 420, a dose planning module 430, and an image fusion module 440.

The acquisition module 410 may be configured to acquire image data. The image data may include PET data, CT data, MRI data, SPECT data, or the like, or any combination thereof. In some embodiments, the acquisition module 410 may acquire the image data from an external source and/or one or more components of the imaging system 100 (e.g., the storage device 150, the detector 112).

The reconstruction module 420 may be configured to reconstruct an image, such as a PET image, a CT image, an MRI image, or the like, or any combination thereof. The reconstruction module 420 may reconstruct an image according to a reconstruction algorithm. Exemplary reconstruction algorithm may include an analytic reconstruction algorithm, an iterative reconstruction algorithm, or a Fourier-based reconstruction algorithm. Exemplary analytic reconstruction algorithms may include a filter back projection (FBP) algorithm, a back-projection filter (BFP) algorithm, a p-filtered layer gram, or the like, or a combination thereof. Exemplary iterative reconstruction algorithms may include a maximum likelihood expectation maximization (ML-EM), an ordered subset expectation maximization (OSEM), a row-action maximum likelihood algorithm (RAMLA), a dynamic row-action maximum likelihood algorithm (DRAMA), or the like, or a combination thereof. Exemplary Fourier-based reconstruction algorithm may include a classical direct Fourier algorithm, a non-uniform fast Fourier transform (NUFFT) algorithm, or the like, or a combination thereof.

In some embodiments, the reconstruction module 420 may correct an image or image data. For example, the reconstruction module 420 may perform an attenuation correction and/or a scatter correction on PET image data based on a maximum likelihood reconstruction of attenuation and activity (MLAA) algorithm. As another example, the reconstruction module 420 may perform an attenuation correction of a PET image based on a CT image.

The dose planning module 430 may be configured to generate a dose plan of a scan (e.g., a CT scan). The dose plan may include information as to how the radiation is delivered to the subject during the scan. For example, the dose plan may include one or more parameters, such as a radiation dose distribution, a radiation duration, a position of a target portion to be radiated, or the like, or any combination thereof. In some embodiments, the dose module 430 may generate a dose plan of a CT scan of a subject based on functional data of the subject. For example, the dose planning module 430 may generate the dose plan based on a PET image, a SPET image, or an MRI image of the subject.

The image fusion module 440 may be configured to fuse a plurality of images. For example, the image fusion module 440 may fuse a functional image (e.g., a PET image, a SPET image, an MRI image) and an anatomical image (e.g., a CT image). The fused image may include both anatomical data and functional data of a subject, may provide more detailed information for diseases diagnose.

In some embodiments, one or more modules illustrated in FIG. 4 may be implemented in at least part of the exemplary imaging system as illustrated in FIG. 1. For example, the acquisition module 410, the reconstruction module 420, the dose planning module 430, and/or the image fusion module 440 may be integrated into a console (not shown). Via the console, a user may set parameters for scanning an object, controlling imaging processes, controlling parameters for reconstruction of an image, viewing reconstructed images, etc. In some embodiments, the console may be implemented via the processing engine 140 and/or the terminal 130.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, the processing engine 140 may include one or more additional modules. For example, the processing engine 140 may further include a control module. The control module may control operations of the acquisition module 410, the reconstruction module 420, the dose planning module 430, and/or the image fusion module 440 (e.g., by generating one or more control parameters). In some embodiments, one or more modules of the processing engine 140 described above may be omitted. For example, the image fusion module 440 may be omitted.

Figure 5:
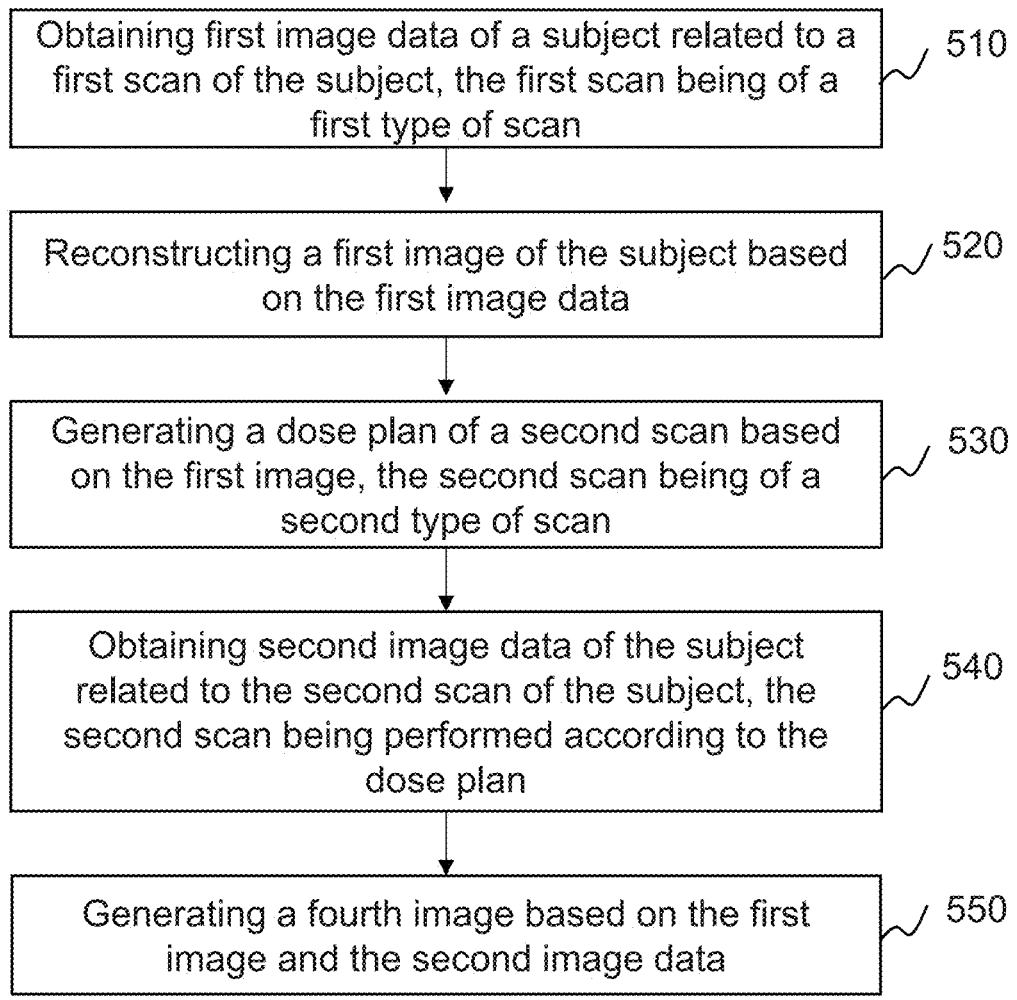
FIG. 5 is a flowchart illustrating an exemplary process for generating an image according to some embodiments of the present disclosure.

FIG. 5 is a flowchart illustrating an exemplary process for generating an image according to some embodiments of the present disclosure. At least a portion of process 500 may be implemented on the computing device 200 as illustrated in FIG. 2 or the mobile device 300 as illustrated in FIG. 3. In some embodiments, one or more operations of the process 500 may be implemented in the imaging system 100 illustrated in FIG. 1. For example, the process 500 may be stored in the storage device 150 in the form of instructions, and invoked and/or executed by the processing engine 140 (implemented on, such as the processor 210 of the computing device 200).

In 510, the acquisition module 410 may obtain first image data of a subject related to a first scan of the subject. The first scan may be of a first type of scan. The subject may be a phantom, a patient, an organ, tissue, or any body part (e.g., a head, a neck, a breast, or an abdomen) of a patient to be scanned. In some embodiments, the first image data may include functional data (e.g., metabolic data) of the subject. The first type of scan may be any type of scan that can be used to collect functional data of the subject. For example, the first image data may include but is not limited to PET data, SPECT data, MRI data, etc. The first type of scan may include but is not limited to a PET scan, a SPECT scan, an MRI scan, etc. In some embodiments, the acquisition module 410 may acquire the first image data from an external source and/or one or more components in the imaging system 100 (e.g., the storage device 150, the detector 112).

In 520, the reconstruction module 420 may reconstruct a first image of the subject based on the first image data. The first image may be a PET image, an SPECT image, an MRI image, or any image including functional data of the subject. The reconstruction module 420 may reconstruct the first image according to a reconstruction algorithm. Exemplary reconstruction algorithm may include an analytic reconstruction algorithm, an iterative reconstruction algorithm, or a Fourier-based reconstruction algorithm. Exemplary analytic reconstruction algorithms may include a filter back projection (FBP) algorithm, a back-projection filter (BFP) algorithm, a p-filtered layer gram, or the like, or a combination thereof. Exemplary iterative reconstruction algorithms may include a maximum likelihood expectation maximization (ML-EM), an ordered subset expectation maximization (OSEM), a row-action maximum likelihood algorithm (RAMLA), a dynamic row-action maximum likelihood algorithm (DRAMA), or the like, or a combination thereof. Exemplary Fourier-based reconstruction algorithm may include a classical direct Fourier algorithm, a non-uniform fast Fourier transform (NUFFT) algorithm, or the like, or a combination thereof.

In some embodiments, the reconstruction module 420 may correct the first image data before reconstructing the first image. The correction of the first image data may include an attenuation correction, a scatter correction, a normalization correction, or the like, or any combination thereof. For example, the reconstruction module 420 may perform an attenuation correction and a scatter correction on the first image data based on a maximum likelihood reconstruction of attenuation and activity (MLAA) algorithm.

In 530, the dose planning module 430 may generate a dose plan of a second scan based on the first image. The second scan may be of a second type of scan. The second type of scan may be any type of scan that can be used to collect anatomical data. For example, the second type of scan may be a CT scan. In some embodiments, the anatomical data collected by the second scan may be applied in an attenuation correction of the first image (or the first image data).

The dose plan may include information as to how the radiation is delivered to the subject during the second scan. For example, the dose plan may include one or more parameters, such as a radiation dose distribution, a radiation duration, a position of a target portion to be radiated, or the like, or any combination thereof. In some embodiments, the dose planning module 430 may analyze the first image to determine radiation doses to be delivered to different portions of the subject during the second scan. For example, the dose planning module 430 may determine at least one region of interest (ROI) enclosing one or more lesions (or potential lesions) in the first image. The dose planning module 430 may also determine the dose plan based on the at least one ROI. The dose plan may include various doses corresponding to the at least one ROI and the region outside the at least one ROI. A dose corresponding to a region (e.g., an ROI) in an image may refer to a dose of the radiation that is planned to be delivered to the portion of the subject corresponding (or substantially corresponding) to the region in the image.

For example, the dose plan may include a low dose corresponding to the region outside the at least one ROI and a high dose corresponding to the at least one ROI. The portion of the subject corresponding to at least one ROI may need a higher dose than the region outside the at least one ROI during the second scan, so that the at least one ROI may have a higher resolution in an image reconstructed based on the second scan to provide more detailed anatomical data related to the lesions. Compared to the at least one ROI, the portion of the subject corresponding to the region outside the at least one ROI may need a relatively lower dose. As such, the portion of the subject corresponding to the region outside the at least one ROI may be prevented from receiving unnecessary radiations. More descriptions regarding the generation of the dose plan may be found elsewhere in the present disclosure (e.g., see FIG. 6 and the relevant descriptions thereof).

In 540, the acquisition module 410 may obtain second image data of the subject related to the second scan of the subject. The second image data may include anatomical data of the subject. The second scan (e.g., a CT scan) may be performed according to the dose plan. For example, as described in connection with 530, the dose plan may include one or more parameters, such as a radiation dose distribution, a radiation duration, a position of a target region to be radiated, etc. The scanning device 110 may perform the second scan according to the one or more parameters. In some embodiments, the dose plan may include a high dose corresponding to the at least one ROI and a low dose corresponding to the region outside the at least one ROI. The scanning device 110 may deliver a higher dose radiation to the portion of the subject corresponding to the at least one ROI than that the portion corresponding to the region outside the at least one ROI. In some embodiments, the high dose corresponding to at least one ROI may be a dose suitable for a diagnostic CT, and the low dose corresponding to the region outside the at least one ROI may be a dose suitable for obtaining anatomical data.

In some embodiments, the acquisition module 410 may acquire the second image data from an external source and/or one or more components in the imaging system 100 (e.g., the storage device 150, the detector 112).

In 550, a fourth image may be generated based on the first image and the second image data. In some embodiments, the fourth image may be a corrected first image generated based on the second image data. For example, the reconstruction module 420 may reconstruct a second image (e.g., a CT image) based on the second image data (e.g., CT data), and correct the first image (e.g., a PET image) based on the second image. Alternatively, the image fusion module 440 may further generate a fused image based on the corrected first image and the second image. The fused image may be designated as the fourth image by the reconstruction module 420 or the image fusion module 440. More descriptions regarding the generation of the corrected first image and/or the fused image may be found elsewhere in the present disclosure (e.g., see FIG. 7 and the relevant descriptions thereof).

It should be noted that the above description of the process 500 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 550 may be omitted.

Figure 6:
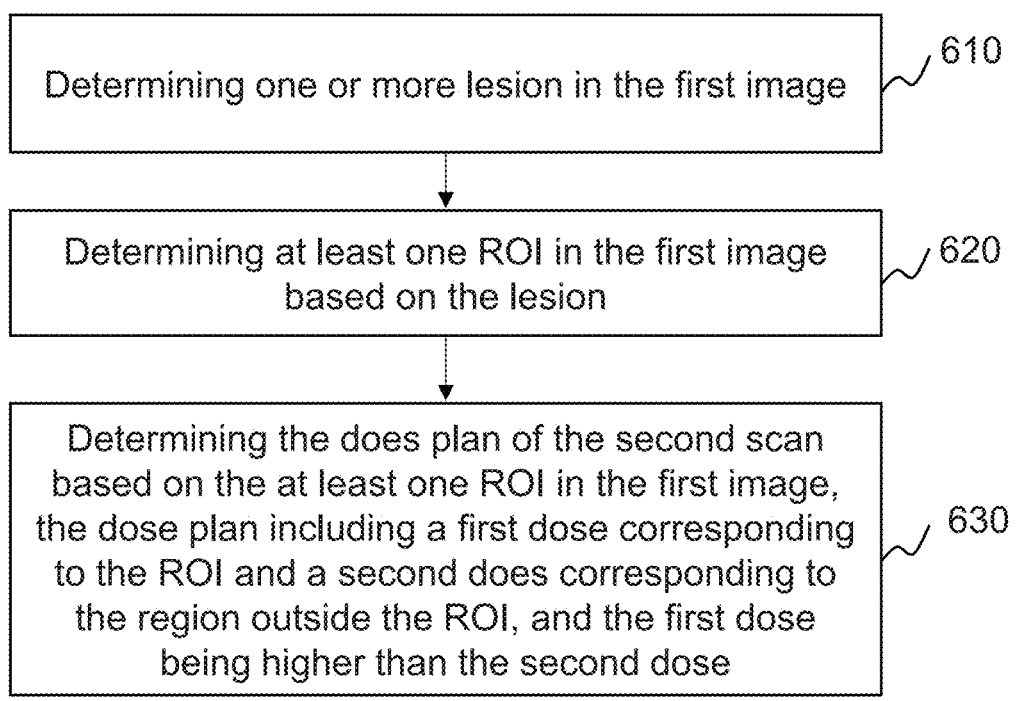
FIG. 6 is a flowchart illustrating an exemplary process for determining a dose plan according to some embodiments of the present disclosure.

FIG. 6 is a flowchart illustrating an exemplary process for determining a dose plan according to some embodiments of the present disclosure. At least a portion of process 600 may be implemented on the computing device 200 as illustrated in FIG. 2 or the mobile device 300 as illustrated in FIG. 3. In some embodiments, one or more operations of the process 600 may be implemented in the imaging system 100 illustrated in FIG. 1. For example, the process 600 may be stored in the storage device 150 in the form of instructions, and invoked and/or executed by the processing engine 140 (implemented on, such as the processor 210 of the computing device 200).

In 610, the dose planning module 430 may determine one or more lesions in the first image. A lesion may refer to an abnormal damage (or potential abnormal damage) or a change (or potential change) in the tissue of a subject. The dose planning module 430 may determine the one or more lesions based on the first image or a Maximum Intensity Projection (MIP) of the first image. For example, the dose planning module 430 may automatically identify and/or mark one or more lesions in the first image (or the MIP of the first image) based on a lesion identification technique. Exemplary lesion identification technique may include a lesion identification technique based on image segmentation, a lesion identification technique based on data clustering, a lesion identification technique based on neighborhood data analysis, or the like, or any combination thereof. Additionally or alternatively, the one or more lesions may be identified and/or marked by a user (e.g., a nurse, a radiologist, a doctor) via a user interface implemented on, e.g., a terminal 130 or a mobile device 300 as illustrated in FIG. 3. For example, a user may mark one or more lesions on the first image (or the MIP of the first image) via the terminal 130. In some embodiments, the dose planning module 430 may mark one or more lesions in the first image (or the MIP of the first image) automatically. The marked first image (or the MIP of the first image) may be displayed to the user via, for example, the terminal 130. The user may check and modify (e.g., delete or add one or more marks of lesions) the marked first image (or the MIP of the first image) via, for example, the terminal 130.

In 620, the dose planning module 430 may determine at least one ROI in the first image based on the identified one or more lesions. An ROI may be a region enclosing at least one lesion. Different ROIs may include the same or different numbers of lesions. An ROI may have any regular shape (e.g., a rectangle, an ellipse, or a circle) or an irregular shape. An ROI may have any size.

In some embodiments, the dose planning module 430 may determine one or more candidate ROIs in the first image based on the identified one or more lesions. A candidate ROI may be a region enclosing at least one lesion. The dose planning module 430 may determine one or more ROIs based on the candidate ROIs. For example, the dose planning module 430 may determine a region enclosing a plurality of candidate ROIs, and the region may further be designated as an ROI. As another example, the dose planning module 430 may determine a coordinate range of voxels (or pixels) in a candidate ROI along a certain direction (e.g., the X-axis, the Y-axis, or the Z-axis as illustrated in FIG. 1). The dose planning module 430 may then determine an ROI in the first image based on the coordinate range. The ROI may include all voxels (or pixels) whose coordinates along the direction are within the coordinate range of voxels (or pixels) in the candidate ROI along the certain direction. Merely by way of example, the dose planning module 430 may determine a range of axial coordinates of voxels (or pixels) in a candidate ROI. The dose planning module 430 may then determine a region including all voxels (or pixels) whose axial coordinates are within the range of the axial coordinates of the candidate ROI. The region may be further designated as an ROI by the dose planning module 430.

In 630, the dose planning module 430 may determine the does plan of the second scan based on the at least one ROI in the first image. The dose plan may include information as to how radiation is delivered to the subject during the second scan. For example, the dose plan may include one or more radiation does corresponding to the at least one ROI. For example, the dose plan may include a first dose corresponding to the at least one ROI and a second does corresponding to the region outside the ROI. The first dose may be higher than the second dose. In some embodiments, the second scan may be a CT scan, a first dose may be a dose suitable for a diagnostic CT, and a second dose corresponding to the region outside the at least one ROI may be a dose suitable for obtaining anatomical data.

In some embodiments, the dose planning module 430 may determine a plurality of ROIs in 620. The dose planning module 430 may determine a plurality of first doses corresponding to the ROIs and a second dose corresponding to the region outside the ROIs. The second dose may be lower than the any of the plurality of first doses. The first doses corresponding to different ROIs may be the same or different. Additionally or alternatively, the dose planning module 430 may determine a plurality of second doses corresponding to different sub-regions in the region outside the ROIs.

In some embodiments, the dose planning module 430 may determine the dose plan (e.g., the first dose and the second dose) based on default settings stored in a storage device (e.g., the storage device 150), or parameters inputted by a user via a terminal 130. Additionally or alternatively, the dose planning module 430 may determine the dose plan based on data analysis. For example, the dose planning module 430 may determine a first dose corresponding to an ROI based on, such as the position of the ROI in the subject, the size of the ROI, the condition of lesions in the ROI, or the like, or any combination thereof.

It should be noted that the above description of the process 600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, 610 and 620 may be combined into one operation.

Figure 7:
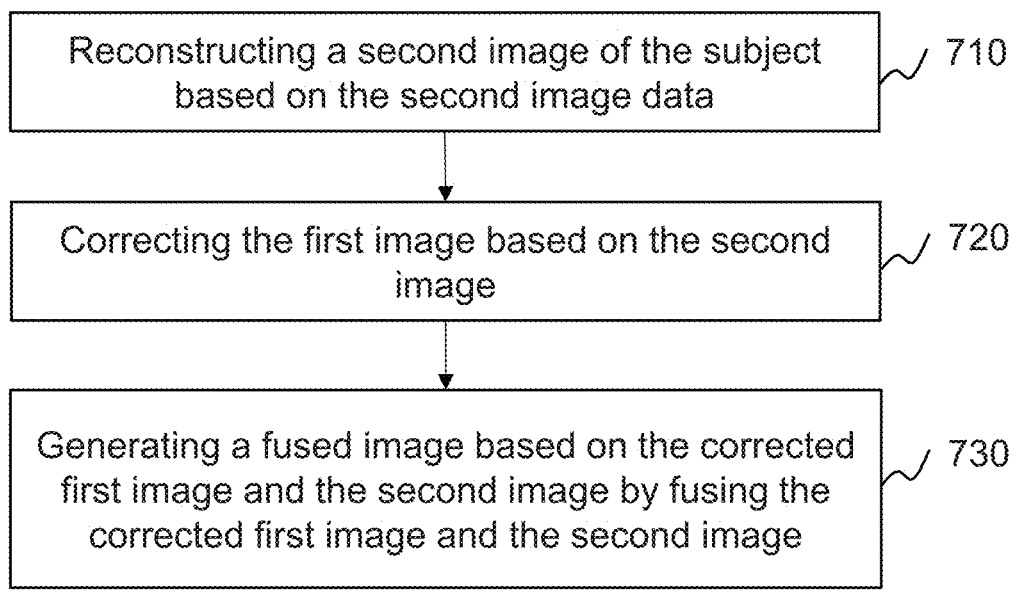
FIG. 7 is a flowchart illustrating an exemplary process for generating a fused image according to some embodiments of the present disclosure.

FIG. 7 is a flowchart illustrating an exemplary process for generating a fused image according to some embodiments of the present disclosure. At least a portion of process 700 may be implemented on the computing device 200 as illustrated in FIG. 2 or the mobile device 300 as illustrated in FIG. 3. In some embodiments, one or more operations of the process 700 may be implemented in the imaging system 100 illustrated in FIG. 1. For example, the process 700 may be stored in the storage device 150 in the form of instructions, and invoked and/or executed by the processing engine 140 (implemented on, such as the processor 210 of the computing device 200). In some embodiments, the process 700 may be performed to achieve operation 550.

In 710, the reconstruction module 420 may reconstruct a second image of the subject based on the second image data. The second image data may include anatomical data of the subject as described in connection with operation 540. In some embodiments, the second image data may be CT data and the second image may be a CT image.

In some embodiments, the reconstruction module 420 may reconstruct the second image based on a reconstruction algorithm. Exemplary reconstruction algorithms may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or any combination thereof.

In 720, the reconstruction module 420 may correct the first image based on the second image. The first image may be a PET image, a SPECT image, an MRI image, or any image including functional data of the subject as described in connection with FIG. 5. The second image may be applied in an attenuation correction of the first image. For example, the first image may be a PET image of a subject and the second image may be a CT image of the subject. The reconstruction module 420 may determine tissue attenuation coefficients corresponding to different portions (e.g., different organs, different tissues) of the subject based on the CT image. The reconstruction module 420 may generate an attenuation map corresponding to the 511 KeV photon rays (e.g., y rays) based on the tissue attenuation coefficients. The reconstruction module 420 may then correct the PET image based on the attenuation map. In some embodiments, the corrected first image may be designated as the fourth image as described in connection with operation 550.

In 730, the image fusion module 440 may generate a fused image based on the corrected first image and the second image by fusing the corrected first image with the second image. For example, the first image may be a PET image and the second image may be a CT image. The fused image may be generated by fusing the corrected PET image and the CT image. The fused image may include both anatomical data and attenuation corrected functional data of the subject, and thereby can provide more detailed information for diseases diagnose.

In some embodiments, the first image and the second image may be acquired by two single scanning device respectively (e.g., a PET device and a CT device). The image fusion module 440 may preprocess the corrected first image and the second image (e.g., registering the two images) before fusing the two images. Alternatively, the first image and the second image may be acquired by a combined scanning device (e.g., a PET/CT device). The image fusion module 440 may generate the fused image without preprocessing the two images. In some embodiments, the fused image may be designated as the fourth image as described in connection with operation 550.

It should be noted that the above description of the process 700 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 730 may be omitted and the process 700 may be performed to generate the corrected first image (e.g., a corrected PET image).

Figure 8:
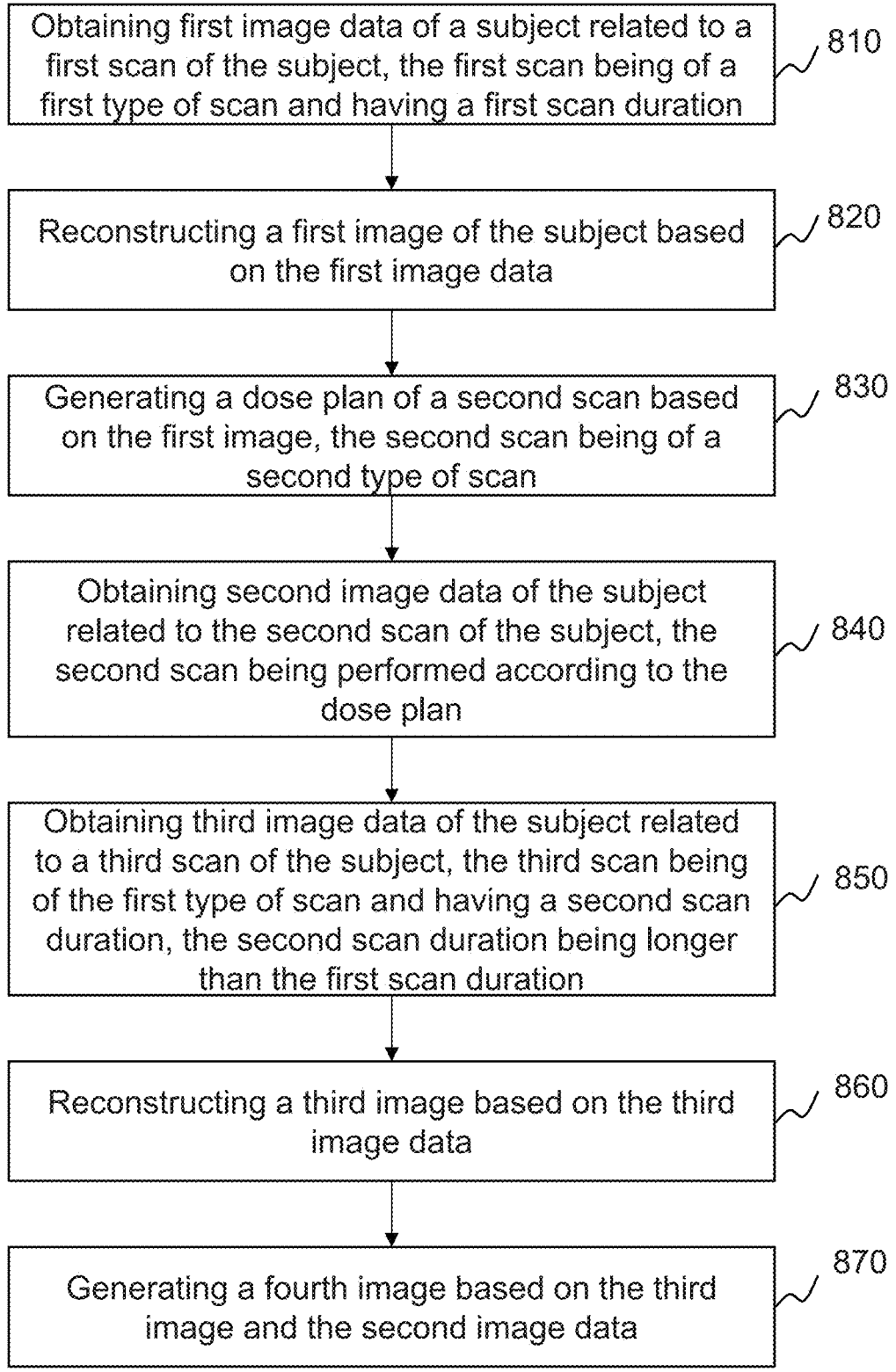
FIG. 8 is a flowchart illustrating an exemplary process for generating an image according to some embodiments of the present disclosure.

FIG. 8 is a flowchart illustrating an exemplary process for generating an image according to some embodiments of the present disclosure. At least a portion of process 800 may be implemented on the computing device 200 as illustrated in FIG. 2 or the mobile device 300 as illustrated in FIG. 3. In some embodiments, one or more operations of the process 800 may be implemented in the imaging system 100 illustrated in FIG. 1. For example, the process 800 may be stored in the storage device 150 in the form of instructions, and invoked and/or executed by the processing engine 140 (implemented on, such as the processor 210 of the computing device 200). In some embodiments, the process 800 may be an embodiment of the process 500.

In 810, the acquisition module 410 may obtain first image data of a subject related to a first scan of the subject. The first scan may be of a first type of scan and have a first scan duration. The first image data may include functional data and the first scan may be any type of scan that can be used to collect functional data of the subject.

In some embodiments, a first image may be reconstructed based on the first image data. The first image may be used to generate a dose plan for a second scan as described in connection with FIG. 5. Compared to an image used in disease diagnose, the first image used to generate a dose plan may need a relatively lower image quality (measured by, for example, an image resolution, a signal-to-noise ratio, or image contrast). In some embodiments, the image quality of the first image may be associated with the first scan duration of the first scan. The first scan may take a shorter period to provide the first image used for dose planning than a normal first scan for diagnoses. In some embodiments, the scan duration of a normal first scan for diagnoses may be associated with physical conditions of the subject (e.g., the age, the weight), hardware conditions of the scanning device 110, parameter settings associated with the scan, or the like, or any combination thereof. Merely by way of example, the first scan may be a whole-body PET scan. A normal first scan for diagnoses may take 45 seconds, and first scan duration of the first scan may range from 15 seconds to 30 seconds.

In 820, the reconstruction module 420 may reconstruct the first image of the subject based on the first image data. In 830, the dose planning module 430 may generate a dose plan of a second scan based on the first image. The second scan may be of a second type of scan configured to acquire anatomical data of the subject. In 840, the acquisition module 410 may obtain second image data of the subject related to the second scan of the subject. The second scan may be performed according to the dose plan. Operations 820 to 840 may be performed in a similar manner to operations 520 to 540 respectively, and the descriptions thereof are not repeated here.

In 850, the acquisition module 410 may obtain third image data of the subject related to a third scan of the subject. The third scan may be of the same type of scan as the first scan, that is, the first type of scan used to acquire functional data of the subject. The second scan duration of the third scan may be longer than the first scan duration, so that the third image data may be reconstructed to generate a higher quality image for diagnoses.

In 860, the reconstruction module 420 may reconstruct a third image based on the third image data. Operation 860 may be performed in a similar manner with operations 820, and the descriptions thereof are not repeated here.

In 870, a fourth image may be generated based on the third image and the second image data. In some embodiments, the fourth image may be a corrected third image or a fused image. The generation of the fourth image based on the third image and the second image data may be similar to that based on the first image and the second image data as described in connection with operation 550 and FIG. 7, and the descriptions thereof are not repeated.

It should be noted that the above description of the process 800 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 870 may be omitted.

Figure 9:
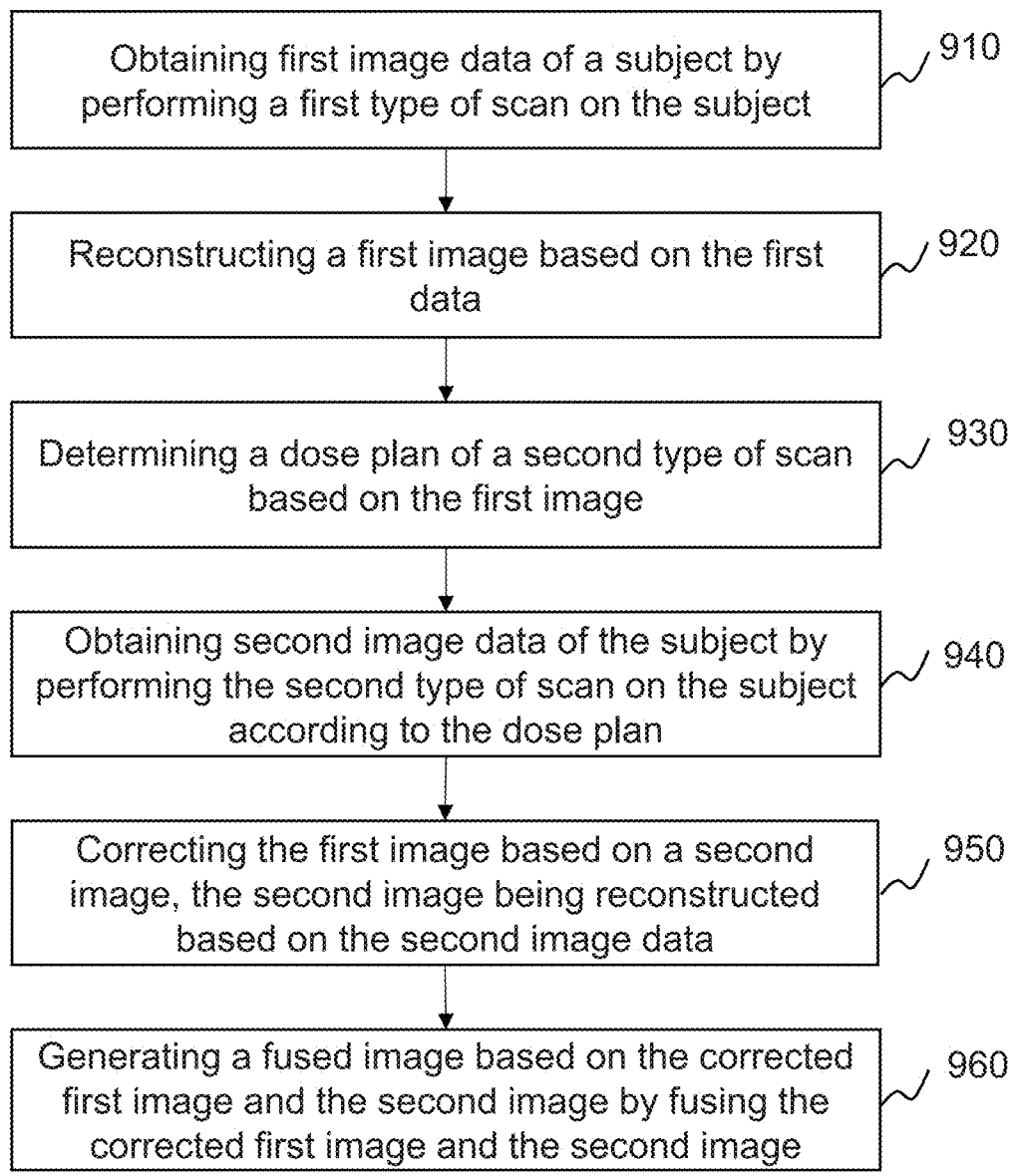
FIG. 9 is a flowchart illustrating an exemplary process for generating an image according to some embodiments of the present disclosure.

FIG. 9 is a flowchart illustrating an exemplary process for generating an image according to some embodiments of the present disclosure. At least a portion of process 900 may be implemented on the computing device 200 as illustrated in FIG. 2 or the mobile device 300 as illustrated in FIG. 3. In some embodiments, one or more operations of the process 900 may be implemented in the imaging system 100 illustrated in FIG. 1. For example, the process 900 may be stored in the storage device 150 in the form of instructions, and invoked and/or executed by the processing engine 140 (implemented on, such as the processor 210 of the computing device 200). In some embodiments, the process 900 may be an embodiment of the process 500.

In 910, the scanning device 110 may perform a first type of scan on a subject to obtain first image data of the subject. In some embodiments, the first image data may be obtained by the acquisition module 410. The first image data may include functional data of the subject and the first type of scan may be any type of scan that can be used to collect functional data of the subject.

In 920, the reconstruction module 420 may reconstruct a first image based on the first data. The first image may be a PET image, an SPECT image, an MRI image, or any image including functional data of the subject. In 930, the dose planning module 430 may determine a dose plan of a second type of scan based on the first image. The second type of scan may be any type of scan that can be used to collect anatomical data of the subject. For example, the second type of scan may be a CT scan. In 940, the scanning device 110 may perform the second type of scan on the subject according to the dose plan to obtain second image data of the subject. In some embodiments, the second image data may be obtained by the acquisition module 410. The second image data may include anatomical data of the subject. For example, the second image data may be CT image data. Operations 920 to 940 may be performed in a similar manner with operations 520 to 540 respectively, and the descriptions thereof are not repeated here.

In 950, the reconstruction module 420 may correct the first image based on a second image. The reconstruction module 420 may reconstruct the second image based on the second image data, and correct the first image based on the second image. More descriptions regarding the reconstruction of the second image and the correction of the first image may be found elsewhere in the present disclosure. See, e.g., FIG. 7 and the relevant descriptions thereof.

In 960, the image fusion module 440 may generate a fused image based on the corrected first image and the second image by fusing the corrected first image with the second image. The fused image may include both anatomical data and attenuation corrected functional data of the subject, and thereby can provide more detailed information for diseases diagnose.

It should be noted that the above description of the process 900 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 960 may be omitted.

Figure 10:
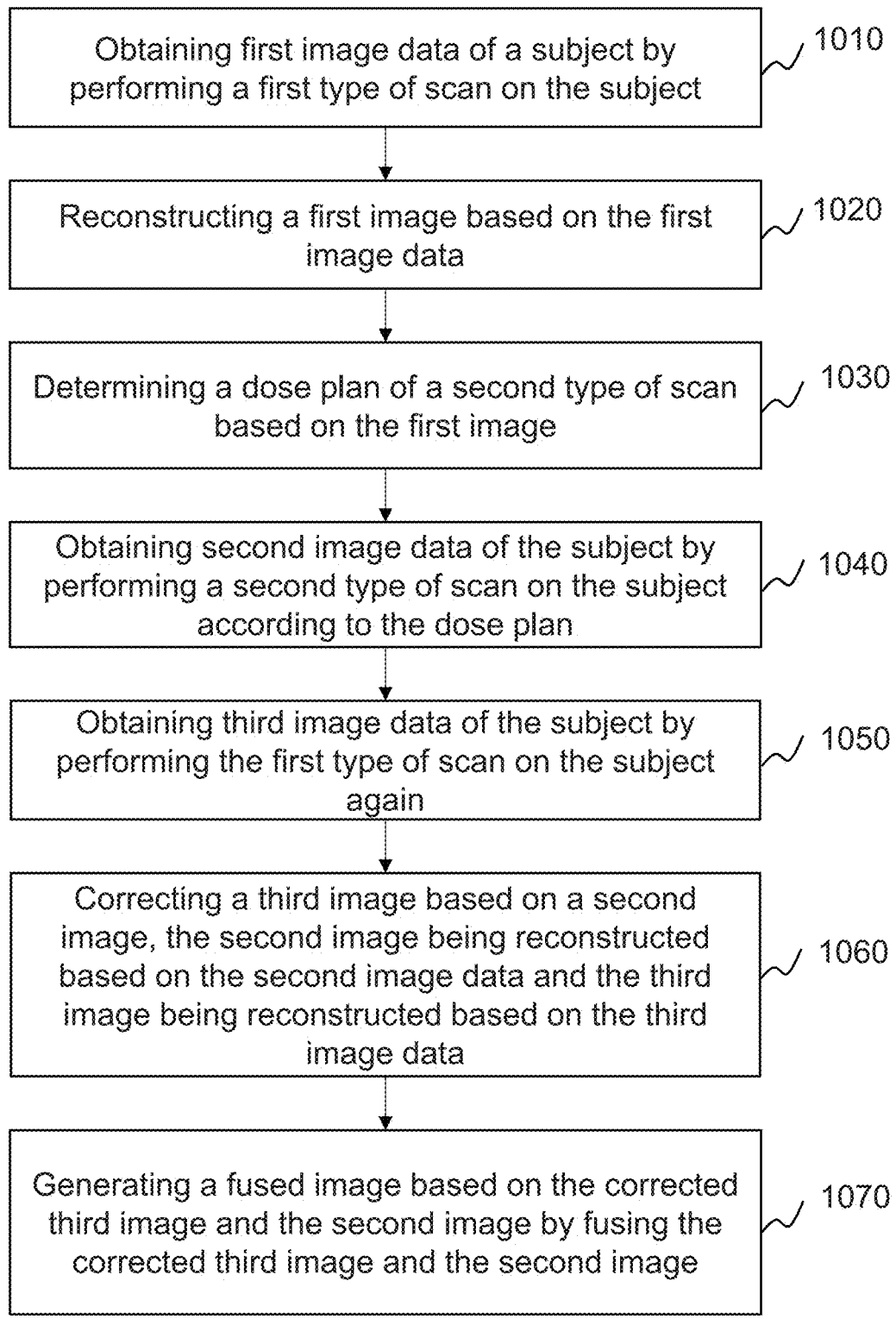
FIG. 10 is a flowchart illustrating an exemplary process for generating an image according to some embodiments of the present disclosure.

FIG. 10 is a flowchart illustrating an exemplary process for generating an image according to some embodiments of the present disclosure. At least a portion of process 1000 may be implemented on the computing device 200 as illustrated in FIG. 2 or the mobile device 300 as illustrated in FIG. 3. In some embodiments, one or more operations of the process 1000 may be implemented in the imaging system 100 illustrated in FIG. 1. For example, the process 1000 may be stored in the storage device 150 in the form of instructions, and invoked and/or executed by the processing engine 140 (implemented on, such as the processor 210 of the computing device 200). In some embodiments, the process 1000 may be an embodiment of the process 800.

In 1010, the scanning device 110 may perform a first type of scan on a subject to obtain first image data of the subject. In some embodiments, the first image data may be obtained by the acquisition module 410. The first image data may include functional data of the subject and the first type of scan may be any type of scan that can be used to collect functional data of the subject. Operation 1010 may be performed in a similar manner with operation 810, and the scanning device 110 may perform the first type of scan on the subject with a shorter scan duration than a normal first scan for diagnoses.

In 1020, the reconstruction module 420 may reconstruct a first image based on the first data. In 1030, the dose planning module 430 may determine a dose plan of a second type of scan based on the first image. In 1040, the scanning device 110 may obtain second image data of the subject by performing the second type of scan on the subject according to the dose plan. Operations 1020 to 1040 may be performed in a similar manner with operations 920 to 940 respectively, and the descriptions thereof are not repeated here.

In 1050, the scanning device 110 may perform the first type of scan on the subject again to obtain third image data of the subject. Compared with operation 1010, the scanning device 110 may perform the first type of scan on the subject for a longer scan duration to acquire high quality image data suitable for diagnoses. Operation 1050 may be performed in a similar manner as operation 850, and the descriptions thereof are not repeated here.

In 1060, the reconstruction module 420 may correct a third image based on a second image. In 1070, the image fusion module 440 may generate a fused image based on the corrected third image and the second image by fusing the corrected third image and the second image. Operations 1060 and 1070 may be performed in a similar manner with operations 950 and 960, and the descriptions thereof are not repeated here.

It should be noted that the above description of the process 1000 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 1070 may be omitted.

Figure 11A:
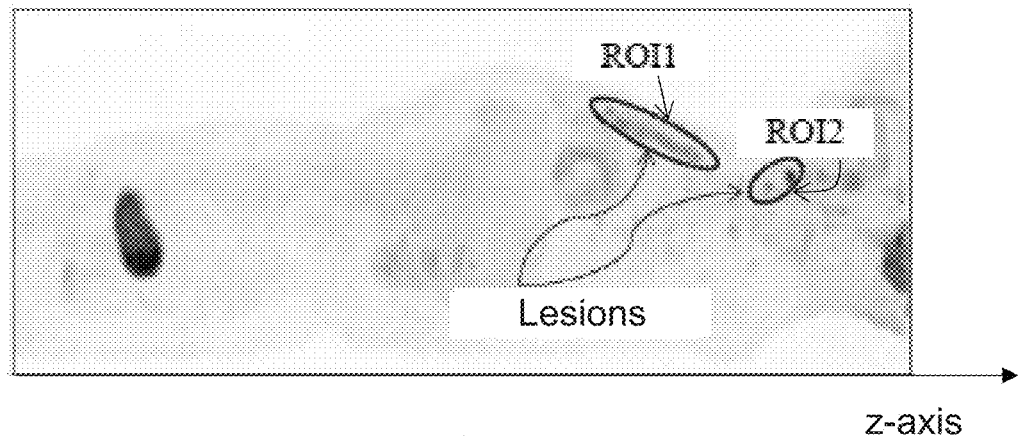
FIG. 11A illustrates exemplary ROIs in a Maximum Intensity Projection (MIP) of a PET image according to some embodiments of the present disclosure.

FIG. 11A illustrates exemplary ROIs in a MIP of a PET image according to some embodiments of the present disclosure. As shown in FIG. 11A, the MIP of the PET image includes an ROI1 and an ROI2. The ROI1 and the ROI2 both enclose one or more lesions (or potential lesions) indicated by dark spots in the MIP. The dose planning module 430 may generate a dose plan based on the ROI1 and the ROI2 in the MIP. For example, the dose plan may include a high dose corresponding to the ROI1 and the ROI2, and a low dose corresponding to the region outside the ROI1 and the ROI2.

Figure 11B:
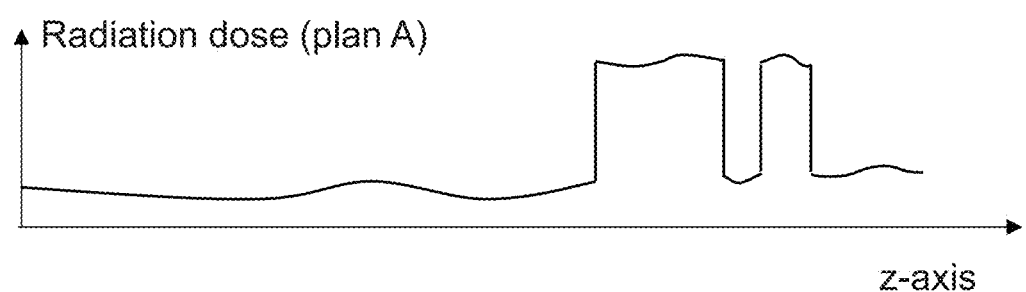
FIGS. 11B and 11C illustrate exemplary dose plans according to some embodiments of the present disclosure.
Figure 11C:
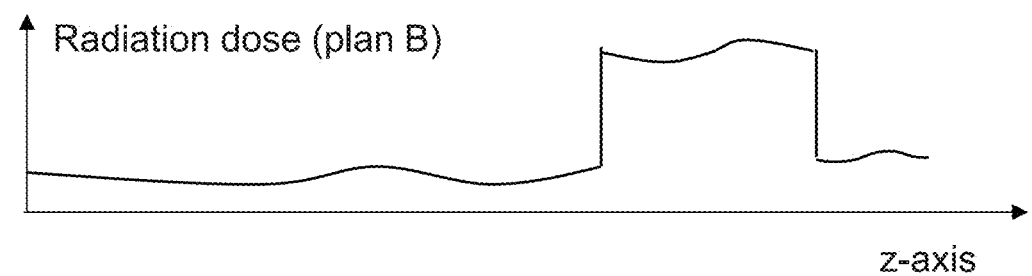

FIGS. 11B and 11C illustrate exemplary dose plans according to some embodiments of the present disclosure. FIG. 11B illustrates a dose plan A and FIG. 11C illustrates a dose plan B. The horizontal axis represents the Z-axis (i.e., the axial direction) and the vertical coordinate represents the radiation dose. The dose plan A and the dose plan B may be determined by the dose planning module 430 based on the ROI1 and the ROI2 illustrated in FIG. 11A. The ROI1 and the ROI2 may be regarded as two candidate ROIs as described in connection with operation 620. The dose planning module 430 may determine a first ROI based on the ROI1 and a second ROI based on the ROI2. The first ROI may include voxels (or pixels) whose axial coordinates are within the range of axial coordinates of voxels (or pixels) in the ROI1, and the second ROI may include voxels (or pixels) whose axial coordinates are within the range of axial coordinates of voxels (or pixels) in the ROI2. The dose plan may be generated based on the first ROI and the second ROI. For example, as illustrated in FIG. 11B, the radiation doses corresponding to the first ROI and the second ROI are higher than those corresponding to the region outside the first ROI and the second ROI. Alternatively, the dose planning module 430 may further determine a third ROI enclosing the first ROI and the second RO. The dose plan may be generated based on the third ROI. For example, as illustrated in FIG. 11C, the radiation doses corresponding to the third ROI are higher than those corresponding to the region outside the third ROI.

It should be noted that the examples illustrated in FIGS. 11A to 11C are merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the dose planning module 430 may determine any number of ROIs in the PET image or the MIP of the PET image. As another example, the dose planning module 430 may determine a dose plan different from the dose plan A and the dose plan B based on the ROI1 and the ROI2.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Per, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method implemented on a computing device including a processor and a storage media, the method comprising:
obtaining first image data of a subject related to a first scan of the subject, the first scan being of a first type of scan;

reconstructing a first image of the subject based on the first image data;
generating a dose plan of a second scan based on the first image, the second scan being of a second type of scan; and
obtaining second image data of the subject related to the second scan of the subject, the second scan being performed according to the dose plan, wherein the generating a dose plan of a second scan based on the first image comprises:
identifying at least one region of interest (ROI) in the first image;
determining the dose plan of the second scan based on the at least one ROI, the dose plan including a first dose corresponding to the ROI and a second dose corresponding to a region outside the ROI, and the first dose being higher than the second dose, the second image data corresponding to the ROI and the region outside the ROI;
reconstructing a second image of the subject based on the second image data; and
performing an attenuation correction on the first image based on the second image.

2. The method of claim 1, wherein the first type of scan is at least one of a positron emission tomography scan, a single photon emission computed tomography scan, or a magnetic resonance scan.

3. The method of claim 1, wherein the second type of scan is a computed tomography scan.

4. The method of claim 1, wherein the identifying at least one ROI in the first image comprises:
determining at least one lesion in the first image; and
determining the at least one ROI in the first image based on the at least one lesion, the at least one ROI enclosing the at least one lesion.

5. The method of claim 4, wherein the determining the at least one ROI in the first image based on the at least one lesion comprises:
determining at least one candidate ROI in the first image based on the at least one lesion, the at least one candidate ROI enclosing the at least one lesion;
determining a coordinate range of the at least one candidate ROI along an axial direction; and
determining the at least one ROI in the first image based on the coordinate range of the at least one candidate ROI along the axial direction.

6. The method of claim 1, further comprising:
generating a fourth image based on the corrected first image and the second image by fusing the corrected first image and the second image.

7. The method of claim 1, wherein the first scan has a first scan duration, and the method further comprises:
obtaining third image data of the subject related to a third scan of the subject, the third scan being of the first type of scan and having a second scan duration, and the second scan duration being longer than the first scan duration;
reconstructing a third image based on the third image data; and
generating a fourth image based on the third image and the second image data.

8. A system, comprising:
at least one storage device storing a set of instructions; and
at least one processor in communication with the at least one storage device, wherein when executing the set of instructions, the at least one processor is configured to cause the system to:
obtain first image data of a subject related to a first scan of the subject, the first scan being of a first type of scan;
reconstruct a first image of the subject based on the first image data;
generate a dose plan of a second scan based on the first image, the second scan being of a second type of scan; and
obtain second image data of the subject related to the second scan of the subject, the second scan being performed according to the dose plan, wherein to generate a dose plan of a second scan based on the first image, the at least one processor is configured to cause the system to:
identify at least one region of interest (ROI) in the first image;
determine the dose plan of the second scan based on the at least one ROI, the dose plan including a first dose corresponding to the ROI and a second dose corresponding to a region outside the ROI, and the first dose being higher than the second dose, the second image data corresponding to the ROI and the region outside the ROI;
reconstruct a second image of the subject based on the second image data; and
perform an attenuation correction on the first image based on the second image.

9. The system of claim 8, wherein the first type of scan is at least one of a positron emission tomography scan, a single photon emission computed tomography scan, or a magnetic resonance scan.

10. The system of claim 8, wherein the second type of scan is a computed tomography scan.

11. The system of claim 8, wherein to identify at least one ROI in the first image, the at least one processor is configured to cause the system to:
determine at least one lesion in the first image; and
determine the at least one ROI in the first image based on the at least one lesion, the at least one ROI enclosing the at least one lesion.

12. The system of claim 11, wherein to determine the at least one ROI in the first image based on the at least one lesion, the at least one processor is configured to cause the system to:
determine at least one candidate ROI in the first image based on the at least one lesion, the at least one candidate ROI enclosing the at least one lesion;
determine a coordinate range of the at least one candidate ROI along an axial direction; and
determine the at least one ROI in the first image based on the coordinate range of the at least one candidate ROI along the axial direction.

13. The system of claim 8, wherein the at least one processor is further configured to cause the system to:
generate a fourth image based on the corrected first image and the second image by fusing the corrected first image and the second image.

14. The system of claim 8, wherein the first scan has a first scan duration, and the at least one processor is further configured to cause the system to:
obtain third image data of the subject related to a third scan of the subject, the third scan being of the first type of scan and having a second scan duration, and the second scan duration being longer than the first scan duration;

reconstruct a third image based on the third image data; and generate a fourth image based on the third image and the second image data.

15. A non-transitory computer readable medium comprising executable instructions that, when executed by at least one processor, cause the at least one processor to effectuate a method, the method comprising:

obtaining first image data of a subject related to a first scan of the subject, the first scan being of a first type of scan;

reconstructing a first image of the subject based on the first image data;

generating a dose plan of a second scan based on the first image, the second scan being of a second type of scan; and obtaining second image data of the subject related to the second scan of the subject, the second scan being performed according to the dose plan, wherein the generating a dose plan of a second scan based on the first image comprises:

identifying at least one region of interest (ROI) in the first image;

determining the dose plan of the second scan based on the at least one ROI, the dose plan including a first dose corresponding to the ROI and a second dose corresponding to a region outside the ROI, and the first dose being higher than the second dose, the second image data corresponding to the ROI and the region outside the ROI;

reconstructing a second image of the subject based on the second image data; and performing an attenuation correction on the first image based on the second image.

16. The non-transitory computer readable medium of claim 15, wherein the identifying at least one ROI in the first image comprises:

determining at least one lesion in the first image; and determining the at least one ROI in the first image based on the at least one lesion, the at least one ROI enclosing the at least one lesion.

17. The non-transitory computer readable medium of claim 16, wherein the determining the at least one ROI in the first image based on the at least one lesion comprises:

determining at least one candidate ROI in the first image based on the at least one lesion, the at least one candidate ROI enclosing the at least one lesion;

determining a coordinate range of the at least one candidate ROI along an axial direction; and determining the at least one ROI in the first image based on the coordinate range of the at least one candidate ROI along the axial direction.

18. The non-transitory computer readable medium of claim 15, the method further comprising:

generating a fourth image based on the corrected first image and the second image by fusing the corrected first image and the second image.

19. The non-transitory computer readable medium of claim 15, wherein the first type of scan is at least one of a positron emission tomography scan, a single photon emission computed tomography scan, or a magnetic resonance scan.

20. The non-transitory computer readable medium of claim 15, wherein the second type of scan is a computed tomography scan.

* * * * *